United States Patent [19]

Demole et al.

[11] 4,099,531
[45] Jul. 11, 1978

[54] FLAVORING INGREDIENT

[75] Inventors: Edouard P. Demole, Coppet; Paul F. Enggist, Geneva, both of Switzerland

[73] Assignee: Firmenich SA, Geneva, Switzerland

[21] Appl. No.: 670,245

[22] Filed: Mar. 25, 1976

[30] Foreign Application Priority Data

Apr. 11, 1975 [CH] Switzerland .......................... 4630/75

[51] Int. Cl.$^2$ .................................................. A24B 3/12
[52] U.S. Cl. ................................... 131/17 R; 131/144; 426/536

[58] Field of Search ......................... 131/2, 144, 15; 426/538

[56] References Cited

U.S. PATENT DOCUMENTS 3,931,250  1/1976  Thomas ............................... 426/536

*Primary Examiner*—Robert W. Michell
*Assistant Examiner*—V. Millin
*Attorney, Agent, or Firm*—Pennie & Edmonds

[57] ABSTRACT

2-Phenyl-3-(fur-2-yl)-prop-2-en-1-al is disclosed as being useful in flavoring both tobacco and tobacco substitute materials as well as foodstuffs and beverages in general.

2 Claims, No Drawings

FLAVORING INGREDIENT

DESCRIPTION OF THE INVENTION

The present invention relates to a flavouring composition comprising as one of its active ingredients a small but flavour-modifying amount of 2-phenyl-3-(fur-2-yl)-prop-2-en-1-al.

The invention relates further to a process for modifying, improving or enhancing the flavouring properties of foodstuffs, feedstuffs, beverages and, more particularly, tobacco products.

It is also an object of the present invention to provide a tobacco or tobacco product having added thereto a flavouring effective amount of 2-phenyl-3-(fur-2-yl)-prop-2-en-1-al.

BACKGROUND OF THE INVENTION

It is well known that the tobacco used, for example, for the manufacture of cigarettes comprises a mixture of different types, to give the characteristic flavour and aroma desired in the smoke produced. Thus, cigarettes currently manufactured usually contain mixtures of Virginia, Maryland of Kentucky tobacco in combination with oriental or Turkish tobacco.

The respective proportions of the various types of tobacco are varied in order to obtain the particular flavour and aroma desired. It is also common practice to employ flavouring substances and humectants as additives to these tobacco mixtures to further enhance the organoleptic properties thereof.

Accordingly, it is an object of the present invention to provide a tobacco or tobacco product having added thereto a small but flavour-modifying quantity of a flavour ingredient, 2-phenyl-3-(fur-2-yl)-prop-2-en-1-al.

We have also surprisingly found that, in view of its specific organoleptic properties, the said compound may find a useful industrial application for the aromatization of a great variety of materials, namely foodstuffs and beverages.

In its pure state 2-phenyl-3-(fur-2-yl)-prop-2-en-1-al possesses a powerful sweet gustative character reminiscent of the taste of honey. This flavouring note is particularly pleasant and appreciated in the art, especially in the field of the aromatization of tobacco. When the compound of the invention is used as a flavouring ingredient in foodstuffs and beverages, it enhances sweet notes analogous to those developed in tobacco products; the aroma thus achieved is reminiscent at the same time of honey and dried fruits, and presents a certain analogy with the flavour character developed by clary-sage.

PREFERRED EMBODIMENTS OF THE INVENTION

2-Phenyl-3-(fur-2-yl)-prop-2-en-1-al may be used in isolated form or, more frequently, in admixture with other flavouring ingredients, excipients or diluents, and may be employed in a variety of forms. The specific nature of the materials to which it is added determines the form in which the given compound, or composition thereof, is to be employed. It is preferable, however, to utilize the said compound or composition in solution in the inert solvents commonly used in the art, such as ethanol, propylene glycol or triacetine.

The proportions of the new compounds to be used in accordance with the invention can vary within wide limits. Said proportions depend particularly on the specific organoleptic effects it is desired to achieve and, of course, on the nature of the materials to which the compound at hand is added. For instance, when the compound of the invention is used as a flavouring ingredient in a tobacco base or a tobacco imitating substrate, its proportions can be from about 10 to about 100 ppm (parts per million) based on the weight of the flavoured material. Preferably, these concentrations are within the range of from 10 to 30 ppm.

When the ingredient of the invention is used for the aromatization of foodstuffs and beverages in general, interesting effects are achieved by concentrations of between about 1 and 10 ppm. In all cases, the ranges given above may be varied, depending upon the specific flavouring effect it is desired to achieve. The term "foodstuff", as used throughout the present specification, has to be interpreted broadly and it is deemed to include, for example, coffee, tea and chocolate. Owing to its particular organoleptic properties, 2-phenyl-3-(fur-2-yl)-prop-2-en-1-al is suitable for the aromatization of solid or liquid foodstuffs such as dairy products, ice-creams, puddings and yoghourts, for example, bakery and confectionery products or fruit juices and syrups.

2-Phenyl-3-(fur-2-yl)-prop-2-en-1-al is a chemical compound already described in the scientific literature and its synthesis can be carried out according to conventional techniques [cf. e.g. Chem. Ber. 90, 1730 (1957)] starting from commercially available materials. Hereinbelow, by way of examplification, there is described one of the processes for its preparation. (The temperatures are indicated in degrees centigrade and the abbreviations have the meaning usual in the art).

48 g (0.5 M) of furfural were added under vigourous stirring to a solution of 5 g of sodium hydroxide in 350 ml of water and 150 ml of ethanol. 70 g (0.584 M) of phenylacetaldehyde were then added over a period of 3 hours to the mixture thus obtained, whereupon the reaction mixture was kept under stirring at 20° for 15 hours. After neutralization with acetic acid, ether extraction and separation of the organic phase, this latter was washed with an aqueous solution of NaCl and subjected to the usual treatments.

The residue obtained by evaporation of the volatile portions was recrystallized with petrol-ether — B.p. 30°–50° — and gave 60.6 g (yield 61%) of the desired aldehyde.

A further purification was effected by sublimation at a temperature of 55° and a pressure of about 0.001 Torr, or alternatively by distillation — B.p. 85°–87°/0.001 Torr — followed by a further crystallization with petrol-ether. A sample thus purified showed the following analytical characters:

m.p. 58.5°–59°

IR (CCl$_4$) : 1680, 1620, 1595, 1465, 1220, 1090 and 1020 cm$^{-1}$;

NMR (CDCl$_3$): 6.20 (1H,d,J=3.5 cps); 6.38 (1H,d of d,J=3.5; J$_1$≅ 1.8 cps); 7.40 (7H,m); 9.75 (1H,s) δ ppm.

The invention is better illustrated by, but not limited to, the following Examples.

EXAMPLE 1

2.5 g of a 1% solution of 2-phenyl-3-(fur-2-yl)-prop-2-en-1-al in 95% ethanol were sprayed onto 100 g of a tobacco mixture of the "American blend" type. The tobacco thus flavoured was then used for the manufacture of "test" cigarettes, the smoke of which was subjected to an organoleptic evaluation by a panel of flavour experts. These latter declared that the smoke of the "test" cigarettes possessed a particularly pleasant sweeter taste when compared with the smoke of "control" cigarettes, the tobacco of which was previously treated with 95% ethanol.

EXAMPLE 2

A base flavouring composition of "vanilla" type was prepared by admixing the following ingredients (parts by weight):

|  |  |
| --- | --- |
| Vanillin | 90 |
| Heliotropin | 25 |
| Vanitrope | 65 |
| Butyric acid at 10%* | 35 |
| Acetoin | 40 |
| Diacetyl | 5 |
| Benzyl alcohol | 340 |
| Propylene glycol | 400 |
| Total | 1000 |

*in 95% ethanol

The above base composition was used for the preparation of the following flavouring compositions (parts by weight):

|  | A (control) | B (test) |
| --- | --- | --- |
| Base composition | 200 | 200 |
| 2-Phenyl-3-(fur-2-yl)-prop-2-en-1-al | — | 5 |
| 95% Ethanol | 800 | 795 |
| Total | 1000 | 1000 |

The "test" composition, when compared with the "control", possessed a well-defined sweetish character reminiscent of the taste and aroma of honey.

This novel composition finds a suitable utilization for the aromatization of ice-creams, puddings and confectionery products in general. For all these applications the preferred concentrations are of the order of 100–200 g of composition for 100 kg of finished foodstuff.

We claim:

1. A smoking tobacco product selected from the group consisting essentially of tobacco and tobacco substitutes which has added thereto a small but flavour-modifying amount of a flavouring compound consisting essentially of 2-phenyl-3-(fur-2-yl)-prop-2-en-1-al.

2. The tobacco of claim 4 wherein 2-phenyl-3-(fur-2-yl)-prop-2-en-1-al has been added in an amount of from about 10 to about 100 parts per million based on the weight of the flavoured tobacco.

* * * * *

UNITED STATES PATENT AND TRADEMARK OFFICE
CERTIFICATE OF CORRECTION

PATENT NO. : 4,099,531
DATED : July 11, 1978
INVENTOR(S) : Edouard P. Demole; Paul F. Enggist It is certified that error appears in the above-identified patent and that said Letters Patent are hereby corrected as shown below:

Column 4, line 23, reads "claim 4", should read --claim 1--.

Signed and Sealed this

Twenty-fourth Day of April 1979

[SEAL]

Attest:

RUTH C. MASON
Attesting Officer

DONALD W. BANNER
Commissioner of Patents and Trademarks